United States Patent [19]

Kling

[11] Patent Number: 4,992,601
[45] Date of Patent: Feb. 12, 1991

[54] PROCESS FOR THE SELECTIVE SEPARATION OF ALKENES AND ALKYNES

[75] Inventor: Mauricio Kling, Munich, Fed. Rep. of Germany

[73] Assignee: Energia Andina Ltd., New York, N.Y.

[21] Appl. No.: 311,157

[22] Filed: Feb. 15, 1989

[51] Int. Cl.$^5$ .............................................. C07C 27/10
[52] U.S. Cl. ...................................... 568/840; 55/274; 208/310 R; 423/245.1
[58] Field of Search ...................... 423/245.1; 585/822, 585/830, 825; 208/310 R; 55/74; 588/840

[56] References Cited

U.S. PATENT DOCUMENTS

| | | | |
|---|---|---|---|
| 2,635,709 | 8/1949 | Archibald et al. | 55/74 |
| 2,866,835 | 8/1956 | Kimberlin et al. | 585/825 |
| 3,219,717 | 11/1965 | Niles | 585/830 |
| 3,273,314 | 9/1966 | Quinn | 55/63 |
| 3,409,691 | 11/1968 | Small | 585/830 |
| 3,979,280 | 9/1976 | Dielacher et al. | 585/830 |
| 4,134,926 | 1/1979 | Tsao et al. | 585/640 |
| 4,393,256 | 7/1983 | Schmidt | 568/907 |

FOREIGN PATENT DOCUMENTS 7605824  2/1975  Netherlands .......................... 585/822

Primary Examiner—Gary P. Straub
Assistant Examiner—Stephen G. Kalinchak
Attorney, Agent, or Firm—Darby & Darby

[57] ABSTRACT

A process for the selective separation of alkenes and/or alkynes from gases obtained by cracking of petroleum products comprising: (a) treating said gases containing at least one alkene and/or at least one alkyne with a macroporous strongly acidic cation exchange resin in its hydrogen form to selectively adsorb said at least one alkene and/or said at least one alkyne; and (b) introducing water, oxygen or an acid in vapor form to simultaneously desorb said at least one alkene and/or said at least one alkyne and to form at least one alcohol, aldehyde, oxide or ester.

13 Claims, No Drawings

PROCESS FOR THE SELECTIVE SEPARATION OF ALKENES AND ALKYNES

The present invention relates to a process for the selective separation of alkenes and/or alkynes from gases obtained by cracking of petroleum products. The compounds obtained can be used directly to produce other organic chemicals, like polyethylene.

It is well known to separate alkenes or alkynes from gases obtained by cracking of petroleum products, for example by dehydrogenation cracking, by means of distillation at high pressures and low temperatures using sophisticated and costly equipment. For example, the gases obtained from cracking of petroleum products are compressed, cooled, liquified and fractionated to produce pure ethylene for polyethylene production.

It is the object of the present invention to provide a simple and less expensive process for the selective separation of alkenes and/or alkynes from gases obtained by cracking of petroleum products.

Said object is achieved by a process which comprises:
(a) treating said gases containing at least one alkene and/or at least one alkyne with a macroporous strongly acidic cation exchange resin in its hydrogen form to selectively adsorb said at least one alkene and/or said at least one alkyne, and
(b) introducing water, oxygen or an acid in vapour form to simultaneously desorb said at least one alkene and/or said at least one alkyne and to form at least one alcohol, aldehyde, oxide or ester.

If an alcohol is obtained in step (b), same can be dehydrated by heating same with aluminium oxide to produce the corresponding alkene in its pure form. Perfluorinated ion-exchange resins may also be used as catalysts at temperatures of up to 200° C. to form alkenes from alcohols.

Compared to the prior art processes, the process of the present invention can be conducted at atmospheric pressure. The gases obtained by cracking of petroleum products are passed directly into the ion exchange system wherein each alkene and/or alkyne is quantitatively adsorbed. Once the catalyst is saturated, steam, oxygen or an acid is introduced into the system to simultaneously desorb said at least one alkene and/or said at least one alkyne and to form at least one alcohol, aldehyde, oxide or ester. For example, with steam, ethylene is hydrated to ethanol, propylene is hydrated to isopropanol and butylene is hydrated to sec-butanol. Acetylene is reacted with acetic acid vapour to vinyl acetate.

If the gases obtained by cracking of petroleum products contain more than one alkene or alkyne, it is preferred that each alkene or alkyne is separately selectively adsorbed in consecutively arranged adsorbers in step (a) and separately desorbed and reacted in step (b). For example, if a mixture of three different alkenes is contained in said gases, each alkene is adsorbed in one of three consecutively arranged adsorbers at specific conditions.

The cation exchange resin which is used as a catalyst in the claimed process is preferably based on polystyrene as matrix and preferably contains sulfonic acid groups. For example, if R—$SO_3H$ is used as cation exchange resin, the following reaction occurs with ethylene:

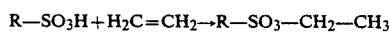

The water content of said catalyst may vary, depending on the respective alkene or alkyne to be separated. For the selective separation of ethylene, the water content of the cation exchange resin is preferably not more than 1% and the adsorption temperature is at least 60° C. Propylene is preferably separated with a cation exchange resin having a water content of from 10 to 25% at a temperature of at least 60° C. The separation of butylene is preferably conducted with a catalyst having a water content of more than 25% at a temperature from ambient temperature up to 25° C. If a mixture of alkenes is separated in the process of the present invention, the conditions in the respective adsorbers used may be adjusted to the above conditions for the separation of a single alkene.

It is to be understood that the above data on the water content of the catalyst and the respective adsorption temperatures will vary with the structure and pore size of the respective catalyst used.

Since the above adsorption reactions in step (a) are exothermic, an appropriate cooling is necessary to control the temperature.

After the adsorption of the alkenes, and/or alkynes, water, oxygen or an acid in vapour form is introduced to simultaneously desorb the alkene and/or alkyne and to form the desired product. The temperatures in step (b) of the process of the present invention are preferably at least 100° C. not exceeding the temperature at which the cation exchange resin degrades.

In the following, a specific embodiment for conducting the process of the present invention is illustrated:

The system comprises a 4-stage fluid bed adsorber and a 2-stage fluid bed desorber.

Once the condensation of $C_5$ and higher organic compounds has been effected with the gases from a cracking unit, said gases are passed through the first of the 4-stage fluid beds, wherein a resin having a water content of 20% adsorbs both butylene and propylene. The remaining gases containing hydrogen, methane and ethylene are then dried and passed through the second of the 4-stage fluid beds which adsorbs all ethylene leaving an exhaust containing hydrogen and methane.

The saturated resin of the first of the 4-stage fluid beds is then treated with steam in the 2-stage fluid bed to regenerate the resin and extract a mixture of isopropanol and sec-butanol, which are easily separated in a rectifying column.

Likewise, the saturated resin of the second of the 4-stage fluidized beds is also steam treated to regenerate the resin and to produce ethanol which is further converted to glycol.

The humid resin is then hot-air dried before it is reintroduced into the 4-layer fluid bed.

Fluidizing velocities for all fluid beds are in the order of one sixth to one tenth of the particles free-falling velocity. Temperatures must not exceed 120° C.

The attrition factor of the resin's particles is far less than that of currently used brittle zeolites due to their elastic nature. The resin's expected life-time is unlimited in fixed-bed operations and, in case of fouling, they can be easily acid-regenerated and dimers are extracted with solvents.

The following examples illustrate the invention.

EXAMPLE 1

150 g of dry, strongly acidic cation exchange resin (matrix cross-linked with approximately 8% DVB (divinyl benzene) with a porosity of 25% and surface (BET) of 25m²/g having an average pore diameter of 400 Å) was mixed in a tube having a controllable temperature with 400 g of quartz sand having a particle diameter of 1 mm. Pure ethylene was then passed through the tube at different rates and temperatures to determine the different adsorption rate. At a temperature of 60° C. and a flux of 22 ml/min, the adsorption of ethylene was complete.

Whan applying different gases, such as ethylene, propylene, butylene and mixtures of butane, propane, methane and hydrogen with alkenes, the same adsorption rates were found. The adsorption rates were constant up to a capacity of 80% of the resin.

EXAMPLE 2

A different resin having the following characteristics was used under similar conditions:
porosity : 25%
surface (BET) : 40 m²/g
average pore diameter : 650 Å
as in Example 1.

The adsorption rates were the same as in Example 1. 150 g of resin completely adsorbed a 35 ml/min flux.

EXAMPLE 3

Gases derived from a high temperature partial oxidation of methane containing 8.1% $C_2H_2$, 25.3% CO, 3.6% $CO_2$, 57.1% $H_2$, 0.5% $N_2$ and 5.4% $CH_4$ were passed through a four-stage fluidized bed containing a macroporous ion-exchange resin having the following characteristics at a 1% humidity:
Strongly acidic, macroporous cation exchange resin in the hydrogen form,
Matrix crosslinked with approximately 8% DVB,
Porosity: approximately 25%
Surface (BET): approximately 25 m²/g
Average port diameter: approximately 400 Å.

The temperature within the fluidized bed adsorber was maintained at 50° C. by refrigeration.

The acetylene-saturated bed was then passed to another fluidized bed reactor where a counter-current of acetic acid vapour at its boiling point regenerated the resin with the formation of vinyl acetate.

Fixed beds may also be used, but the temperature control of the exothermic adsorption is better in fluidized beds.

I claim:

1. A process for the separation of alkenes and alkynes from a gas of the type obtained by cracking petroleum products comprising the steps of
    (a) contacting said gas containing at least two of said alkenes or alkynes with at least two consecutively arranged adsorbers, each of said adsorbers comprising the hydrogen form of a macroporous strongly acidic cation exchange resin, said contacting step selectively promoting the adsorption of one of said alkenes or alkynes to each of said adsorbers, and
    (b) desorbing the adsorbed alkenes or alkynes from each of said adsorbers by contacting said adsorbers with a member from the group consisting of water, oxygen and an acid in vapor form to form at least one member from the group consisting of an alcohol, an aldehyde, and an ester.

2. The process of claim 1, wherein said gas comprises the alkenes, ethylene, propylene and butylene, which comprises adsorbing each of said alkenes in separate adsorbers and desorbing said alkenes from said adsorbers to form ethanol, isopropanol and sec-butanol, respectively.

3. The process of claim 1, wherein said contacting step comprises contacting said gas with a polystyrene-based cation exchange resin.

4. The process of claim 1, wherein said cation exchange resin contains sulfonic acid groups.

5. The process of claim 1, wherein said cation exchange resin is a perfluorinated cation exchange resin.

6. The process of claim 1 which comprises selectively adsorbing ethylene on one of said adsorbers having a water content of not more than 1%.

7. The process of claim 6, wherein the temperature of said one adsorber is at least 60° C. in step (a).

8. The process of claim 1, characterized in that the temperature of said adsorbers in step (b) is at least 100 C. and said temperature does not exceed the temperature at which said cation exchange resin degrades.

9. A process for the selective separation of propylene from a gas of the type obtained by cracking petroleum products comprising the steps of
    (a) contacting said gas with an adsorber comprising the hydrogen form of a macroporous strongly acidic cation exchange resin, said resin having a water content of from 10% to 25%, said contacting step selectively promoting the adsorption of said propylene to said adsorber, and
    (b) desorbing said adsorbed propylene from said adsorber by contacting said adsorber with a member of the group consisting of water, oxygen or an acid in vapor form to form at least one member from the group consisting of an alcohol, an aldehyde, and an ester.

10. The process of claim 9, wherein the temperature in step (a) is at least 60° C.

11. A process for the selective separation of butylene from a gas of the type obtained by cracking petroleum products comprising the steps of
    (a) contacting said gas with an adsorber comprising a macroporous strongly acidic cation exchange resin in its hydrogen form, said resin having a water content of more than 25%, said contacting step selectively promoting the adsorption of said propylene to said adsorber, and
    (b) desorbing said adsorbed butylene from said adsorber by contacting said adsorber with a member of the group consisting of water, oxygen or an acid in vapor form to form at least one member from the group consisting of an alcohol, an aldehyde, or an ester.

12. The process of claim 11, wherein the temperature in step (a) is from ambient temperature up to 25°C.

13. A process for the selective separation of alkenes and/or alkynes from gases of the type obtained by cracking of petroleum products comprising
    (a) treating said gases containing at least one alkene and/or at least one alkyne with the hydrogen form of a macroporous perfluorinated ion exchange resin to selectively adsorb said at least one alkene and/or said at least one aklyne and
    (b) introducing water, oxygen or an acid in vapor form to simultaneously desorb said at least one alkene and/or said at least one alkyne from said resin and to form at least one alcohol, aldehyde, or ester.

* * * * *